United States Patent [19]

Okino et al.

[11] 4,412,545

[45] Nov. 1, 1983

[54] ELECTROMAGNETIC BLOOD FLOWMETER

[75] Inventors: Haruka Okino, Tokyo; Keitkitsu Ogawa, Tokorozawa; Sunao Takeda, Ichikawa; Hiromichi Mohri, Fujimi; Shigeru Hiraide, Tokyo, all of Japan

[73] Assignee: Nihon Kohden Corporation, Tokyo, Japan

[21] Appl. No.: 277,115

[22] Filed: Jun. 25, 1981

[30] Foreign Application Priority Data

Jul. 2, 1980 [JP] Japan ................................ 55-89177

[51] Int. Cl.³ .............................................. A61B 5/02
[52] U.S. Cl. ................................. 128/691; 73/861.17
[58] Field of Search .............................. 128/691, 692; 73/861.16, 861.17

[56] References Cited

U.S. PATENT DOCUMENTS 3,759,247 9/1973 Doll et al. ..................... 73/861.17 X
3,809,070 5/1974 Doll et al. ..................... 73/861.17 X

OTHER PUBLICATIONS

Kanai, "Electromagnetic Blood Flowmeter . . . ", J. Soc. Inst. Contr. Eng. (Japan), vol. 9, No. 9, Sep. 1970, pp. 1-16.
Kanai et al., "Trans. Blood Flow Measurement . . .".
IEEE Trans. Biomed Eng., vol. BME-21, No. 2, pp. 144-151, Mar. 1974.

*Primary Examiner*—Lee S. Cohen
*Attorney, Agent, or Firm*—Scully, Scott, Murphy & Presser

[57] ABSTRACT

In an electromagnetic blood flowmeter, the blood flow is excited by an alternating rectangular magnetic field with a non-excitation period between each excitation period and the blood flow signal is produced by subtracting the sampled output signal for the non-excitation period from one for the excitation period directly before or after said non-excitation period, wherein both sampling points of the excitation and non-excitation periods are determined possibly close to each other so that ECG signals are effectively eliminated without hightening the exciting frequency. The transformer component also superposed on the blood flow signal is extracted by subtracting the blood flow signal with no transformer component obtained by the known method from said blood flow signal with no ECG signal and averaging the subtracted signal. Thus, pure blood flow signal is also produced by subtracting the extracted transformer component from said blood flow signal with no ECG signal.

3 Claims, 7 Drawing Figures

ELECTROMAGNETIC BLOOD FLOWMETER

FIELD OF THE INVENTION

We are concerned with an electromagnetic blood flowmeter for producing blood flow signals in such a manner that by an exciter coil the blood flow is excited with an alternating magnetic field of rectangular waves. The induced voltage corresponding to the velocity of the blood flow is detected by detector electrodes and then the induced voltage is demodulated.

BACKGROUND OF THE INVENTION

It is well known that this type of blood flowmeter causes the blood flow in the magnetic field to induce a voltage on the detector electrodes on the basis of Faraday's law. Usually the transformer component is superposed on the detected signals due to the occurrence of the cross field in the lead lines of the detector electrodes by the exciter coil. Also ECG signals directly induced on the detector electrodes are mixed therein independently of the excitation, as shown in FIG. 1. Such an ECG signal has a lower frequency component as compared with the carrier of the blood flow signal, and, therefore, can be eliminated through a high-pass filter. But, the influence on the blood flow signal is inevitable when a large amount of reduction is intended. From this point of view, if the blood flow signal is synchronous-detected in addition to a proper high-pass filtering, the ECG signal may be substantially eliminated, since it is asynchronous with the carrier of the blood flow signal and has the lower frequency component as compared with the carrier. However, in this case, when the ECG signal level is so high as to saturate in the amplifier of the preceding stage, the detected DC blood flow signal vanishes as the case may be and furthermore the transformer component steadily superposed may vanish together with the ECG signal.

On the other hand, circuits are known for only eliminating the transformer component from the blood flow signal. Therefore, in any method where only the ECG signal is effectively eliminated, a pure blood flow signal will be obtained.

SUMMARY OF THE INVENTION

Accordingly, it is a primary object of this invention to provide an electromagnetic blood flowmeter of the alternating magnetic field type of rectangular wave which enables remarkable reduction in only ECG signals independent of the levels thereof.

Another object of the invention is to provide an electromagnetic blood flowmeter of the alternating magnetic field type of rectangular wave which enables production of a blood flow signal including neither ECG signal nor transformer component.

In order to solve the above-mentioned objects, this invention is based on the conception that a non-excitation period is interposed between each excitation period, whereby the blood flow signal is obtained by subtracting the output signal for the non-excitation period from one for the excitation period directly before or after said non-excitation period. A higher exciting frequency, produces a subtracted component of the ECG signal closer to zero, but often there exists restriction on the heightening thereof from other aspects. For instance, when the transformer component for the excitation period is cancelled by the compensating signal, which is generated on the basis of the transformer component for the non-excitation period (described after in detail), it is necessary to restrict the exciting frequency up to about 250 Hz in order to obtain the precise subtraction independent of the density of blood so that the zero level is kept stable. Therefore, when this invention is incorporated in such a circuit, the exciting frequency is naturally restricted.

Accordingly, this invention is characterized in that a pair of sampling pulses of excitation and non-excitation periods are chosen close to each other for the sake of cancellation of ECG signal (e.g., end portion for the non-excitation period and possibly forward point or a point spaced from the end portion allowable for the superposition of the transformer component for the excitation period, or end portion for excitation period and possibly forward point or a point spaced from the end portion for the non-excitation period). Additionally, the transformer component is produced by the transformer-component extracting circuit, and thus pure blood flow signals are produced by subtracting the transformer component from blood flow signals including no ECG signal.

BRIEF DESCRIPTION OF THE DRAWINGS

These and other objects, features and advantages of the present invention, as well as the invention itself, will become more apparent from the following description of the preferred embodiment of the present invention taken in conjunction with the accompanying drawings wherein.

DESCRIPTION OF THE PREFERRED EMBODIMENTS

Figure 1:
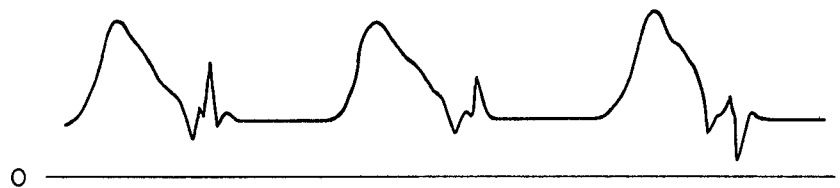
FIG. 1 shows typical waveforms of blood flow signals detected by an electromagnetic blood flowmeter.
Figure 2:
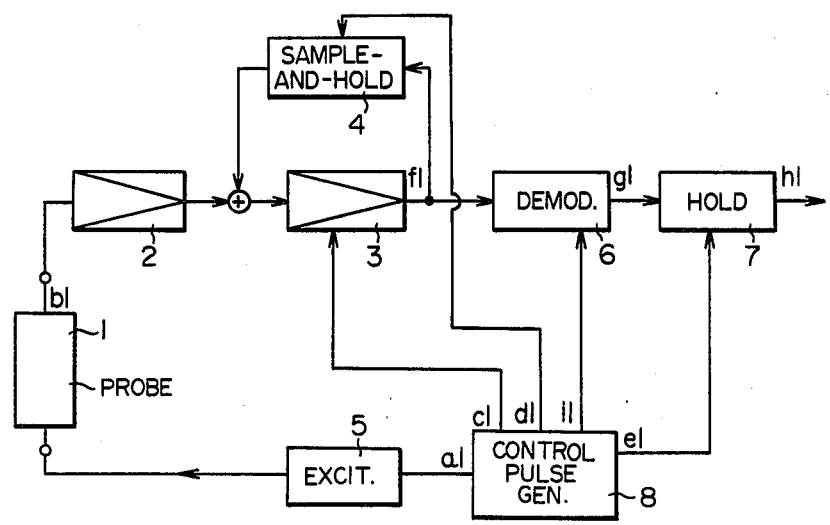
FIG. 2 shows a block circuit diagram of the embodiment of the ECG signal eliminator this invention.
Figure 3:
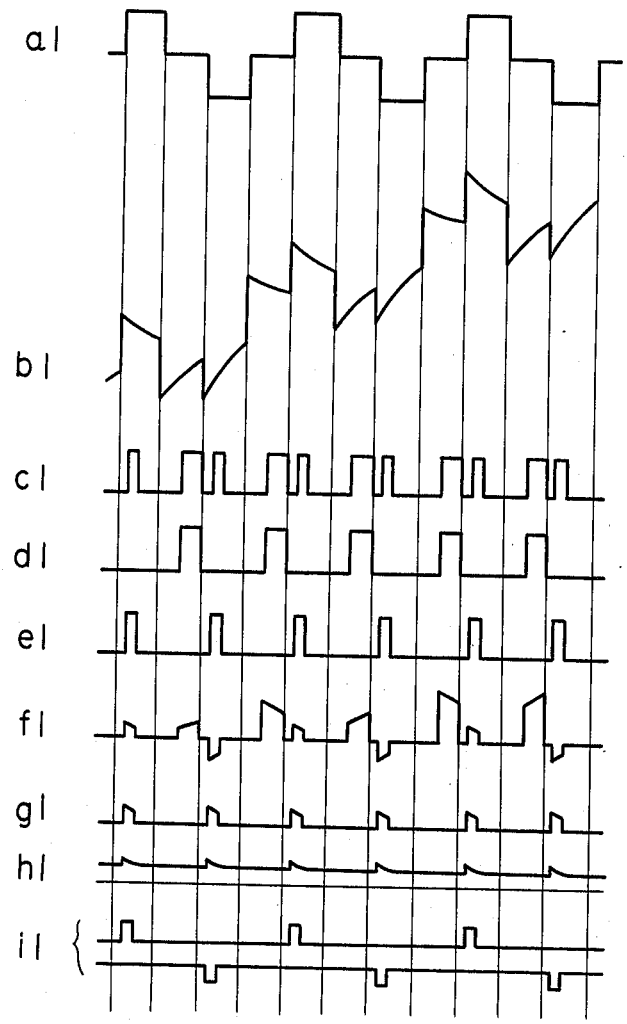
FIG. 3 shows operational waveforms of each block circuit in FIG. 2.

FIG. 2 and FIG. 3 relate to one embodiment of the electromagnetic blood flowmeter in accordance with this invention. In FIG. 2 showing the block circuit diagram of the embodiment, 1 indicates a probe which includes an exciter coil for applying an alternating rectangular magnetic field with non-excitation periods interposed between each excitation period to the blood flow; and detector electrodes for detecting the induced voltage thereby. 2 indicates a buffer amplifier for the probe 1, of which output impedance may deviate. 3 indicates a sampling amplifier having a sampling and amplifying functions. 4 indicates a sample-and-hold circuit for ECG signals in the non-excitation periods. 5 indicates an exciting circuit for driving the exciter coil of the probe 1. 6 indicates a demodulation circuit for synchronous-detecting the blood flow. 7 indicates a hold circuit for producing the envelope of the detected output signals of the demodulation circuit 6. 8 indicates a control pulse generator circuit which produces excitation control pulse a1, sampling pulses c1, ECG-signal holding pulses d1, blood-flow-signal holding pulses e1 and synchronous detection pulses i1 (FIG. 3) in order to control the above-mentioned circuits, respectively. Therein, the excitation control pulse a1 has a higher frequency e.g. 250 Hz as compared with the frequency component of the blood flow signal or ECG signal and the timing of the sampling pulses c1 is determined so as to sample the end portion of the non-excitation period and the central portion of the excitation period. In this manner the ECG signal is effectively eliminated and the mixture of the transformer component to the low level is suppressed.

The operation of the electromagnetic blood flowmeter constituted as aforementioned is hereinafter explained referring to FIG. 3.

When the excitation-control pulse a1 is applied to the exciting circuit 5, a magnetic field is supplied to the blood flow from the exciter coil of the probe 1 so that the induced voltage corresponding to the velocity of the blood flow is detected on the detector electrodes of the probe 1. At the time when an ECG signal is generated, the induced voltage b1 (output signal of the probe 1) including the ECG signal superposed on the transformer and blood flow component corresponding to the excitation control pulse a1 is supplied to the sampling amplifier 3 through the buffer amplifier 2. In the sampling amplifier 3, signals in the end portion of the non-excitation period and the central portion of the excitation period are respectively sampled and amplified by the sampling pulse c1 without incurring the saturation of the peak edge of each rectangular wave, wherein the signal on the non-excitation period is held in the sample-and-hold circuit 4 by the ECG-signal holding pulse d1 and added to the input of the sampling amplifier 3 after the inversion and the adjustment of the amplitude. Consequently, the signal sampled in the central portion of the directly succeeding excitation period by the sampling pulse c1 is free of the ECG signal by virtue of subtraction. Such a sampling amplifier output f1 is synchronously detected by the synchronous detection pulse i1 corresponding to the sampling pulse c1 in the demodulation circuit 6. Thus, the detection output g1 is produced, which is held by the blood-flow-signal holding pulse e1 thereby producing the hold circuit output h1 in the hold circuit 7. Such a hold circuit output h1 scarcely includes the ECG signal which is the slant component of the induced voltage b1. Thus, by eliminating the basic frequency component of the sampling (carrier) through a low-pass filter, the blood flow signal on which the DC transformer component is superposed is derived.

FIGS. 4-7 show the second embodiment of this invention, in which by utilizing the first embodiment, the transformer component superposed on the blood flow signal as well as the ECG signal can be eliminated.

Figure 4:
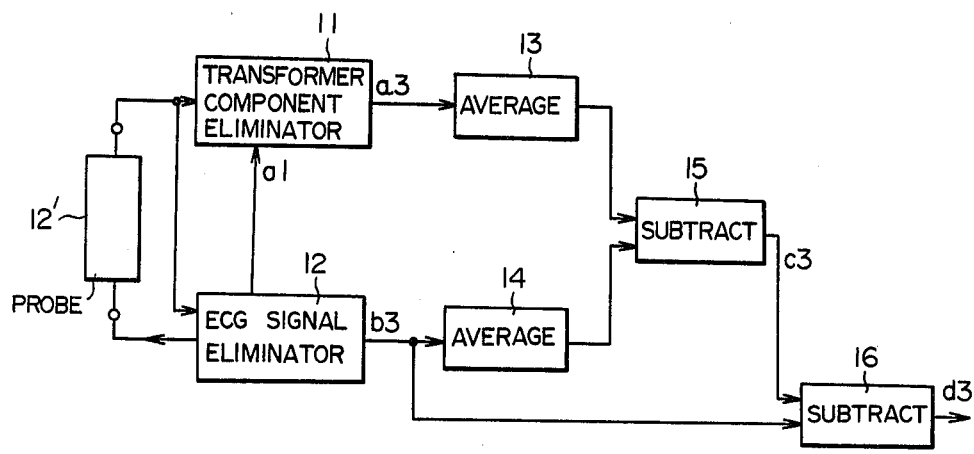
FIG. 4 shows a whole block circuit diagram of the embodiment of this invention.

FIG. 4 shows the basic circuit constitution of this second embodiment, wherein 11 indicates a transformer-component eliminator, 12 an ECG signal eliminator corresponding to the first embodiment together with a probe 12', 13 a mean value circuit composed of an integrator circuit, 14 a similar mean value circuit, 15 a subtractor circuit for subtracting the output signals of the value circuit 13 from the output signals of the mean value circuit 14 and 16 a subtractor circuit for subtracting the output signals of the subtractor circuit 15 from the output signals of the ECG signal eliminator 12.

Figure 5:
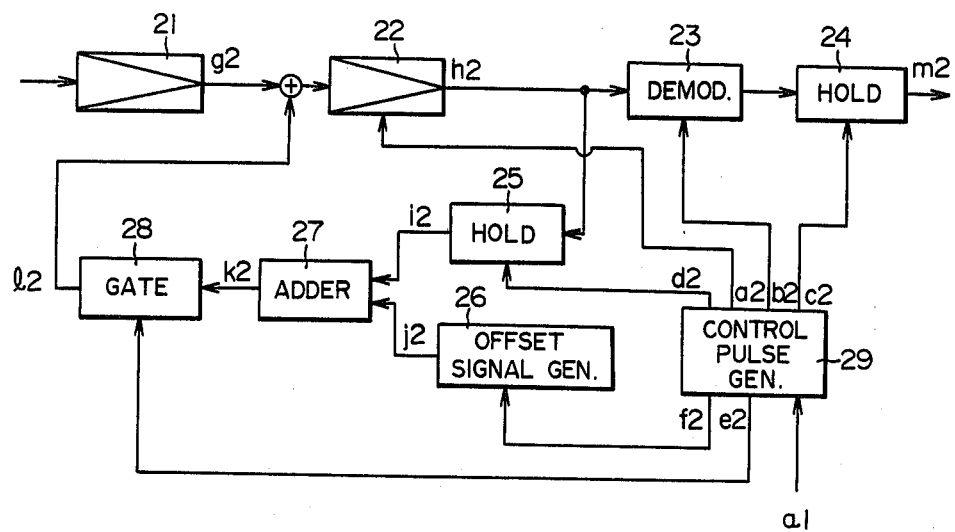
FIG. 5 shows a block circuit diagram of the transformer component eliminator 11 out of the block circuit in FIG. 4.

The transformer component eliminator 11 may be constituted in accordance with applicants' Japanese patent publication No. 54-39750 as shown in FIG. 5, wherein 21 indicates a buffer amplifier, 22 a sampling amplifier of the induced voltage, 23 a demodulation circuit for synchronous detection, 24 a hold circuit for producing the envelope of detected output signals, 25 a hold circuit for holding the transformer components of the output signals of sampling amplifier 22 for the non-excitation period, 26 an offset signal generator circuit which generates the offset voltage for compensating the real offset voltage, 27 an adder circuit for adding the offset compensating signal to the transformer component and 28 a gate circuit for controlling the feed back of output signals of adder circuit 27 to the sampling amplifier 22. Additionally, 29 indicates a control pulse generator circuit for controlling the above-mentioned circuits by generating sampling pulses a2 which are synchronous with the excitation control pulses a1, synchronous detection pulses b2, blood-flow-signal holding pulses c2, transformer-component holding pulses d2, gate pulses e2 and offset compensating pulses f2.

Figure 6:
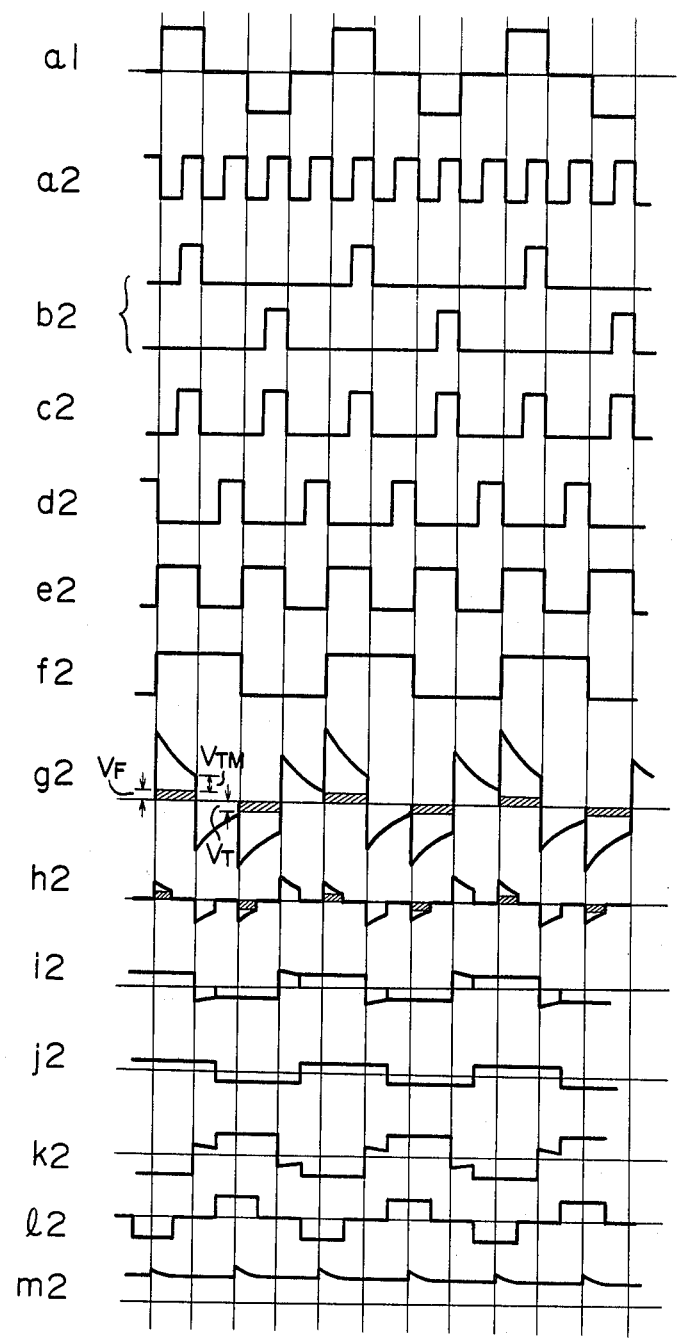
FIG. 6 shows operational waveforms of each block circuit in FIG. 5.

The operation of the transformer-component eliminator 11 constituted as aforementioned is hereinafter explained referring to FIG. 6.

The induced voltage detected by the detectors electrodes of the probe 12' is supplied to the sampling amplifier 22 through the buffer amplifier 21. With respect to the waveform of this induced voltage g2, assuming that $V_{TM}$ is the transformer component for the excitation period and $V_T$ is the transformer component for the non-excitation period, there exists the following relation.

$$V_T = KV_{TM} + V_O \qquad (1)$$

wherein K is the constant of proportion and $V_O$ is the offset voltage.

Consequently, from the formula (1)

$$V_{TM} = (V_T - V_O)/K \qquad (2)$$

and thus, $V_{TM}$ can be obtained by detecting $V_T$. Therefore, as described hereinafter in detail, the almost pure blood flow signal which corresponds to the blood flow signal component can be produced in such a manner that the induced voltage g2 sampled in the excitation period is subtracted by $V_{TM}$.

Namely, the signal which is sampled for the non-excitation period in accordance with the sampling pulse a2 in the sampling amplifier 22 is sampled and held by the transformer-component holding pulse d2 in the hold circuit 25, of which transformer-component holding output i2 is supplied to the adder circuit 27 after the amplitude adjustment onto $V_T/K$ of the formula (2) in terms of the input of sampling amplifier 22. On the other hand, the offset compensating signal j2 which is synchronous with the offset compensating pulse f2 and similarly adjusted in amplitude onto $-V_O/K$ is also supplied to the adder circuit 27 from the offset signal generator circuit 26. Thus, from the adder circuit 27, the inverted adder output k2 corresponding to $-(V_T - V_O)/K$ is supplied to the gate circuit 28 in which the gate output l2 is generated in synchronization with the gate pulse e2 and added to the input of the sampling amplifier 22.

Consequently, the blood flow signal of the sampling amplifier output h2 for the excitation period is free of the transformer component and synchronous-detected by the synchronous detection pulse b2 in the demodulation circuit 23 so that the hold circuit output m2 of which level corresponds to the velocity of the blood flow is produced by the holding pulse c2 from the hold circuit 24.

Figure 7:
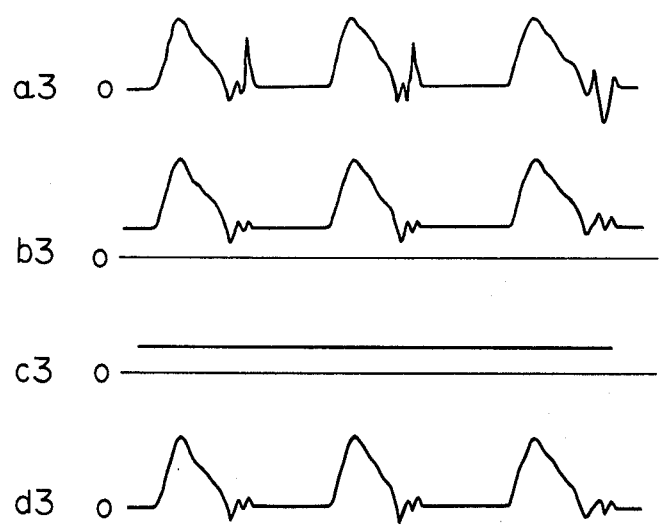
FIG. 7 shows operational waveforms of each block circuit in FIG. 4.

This hold circuit output m2 which further passes through a low pass filter can be as represented in FIG. 7, a3 by compressing the time axis. That is to say, such blood flow signals with the transformer component almost eliminated. But periodic ECG signals mixed under unnegligible amplitude are obtained. On the other hand, the hold circuit outputs h1 in the ECG signal eliminator 12, as previously described, are blood flow signals with the ECG signals almost eliminated, but include the transformer component as shown in FIG. 7, b3.

Thus, both filtered output signals a3, b3 of hold circuits 7, 24 are supplied to the mean value circuits 13 and 14, respectively, whereby the averaged transformer component c3 is produced by subtracting the output signals of the mean value circuit 13 from the output signals of the mean value circuit 14 in the subtractor circuit 15. Upon averaging in the mean value circuit 13 the ECG signals are also averaged, but the averaged output level thereof is negligible as compared with the averaged output level of the transformer component. In the subtractor circuit 16, such pure blood flow signals d3 that scarcely include transformer component nor ECG signals are produced.

The circuit for extracting the transformer component in FIG. 4, namely the mean value circuits 13, 14 and subtractor circuit 15 is replaced with a subtractor circuit for subtracting the filtered output signals of the hold circuit 24 from those of the hold circuit 7 and a mean value circuit for averaging the output signals of said subtractor circuit. The subtraction for cancelling the transformer component can be also performed by holding the output signal of the excitation period and subtracting it from that of the directly succeeding non-excitation period. This embodiment intends the elimination of the transformer component superposed on the blood flow signal sampled in the ECG-signal eliminator 12. Therefore, the timing of the sampling for the excitation period can be shifted further forward than in the first embodiment so as to decrease the error due to the difference of the timing of sampling. This is for the purpose of improvement in the elimination effect of ECG signals without increasing the transformer component.

As is clear from the foregoing, according to the successive subtraction of ECG signal at each period, ECG signals having small or large amplitude can be eliminated without influencing on the blood flow signals or transformer components included at each sampling point. In this manner a higher-level cancellation effect, equivalent to hightening the exciting frequency, is obtained by setting a pair of sample timings for excitation and non-excitation period possibly close to each other. Therefore, such an ECG signal eliminator system further enables the production of excellent pure blood flow signals in cooperation with the transformer-component eliminator system which permits the elimination of the transformer component of the blood flow signal, but is subject to restriction on exciting frequency when it is intended to obtain the high-level cancelllation effect thereof.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. An electromagnetic blood flowmeter comprising: means for exciting an excitor coil with alternating rectangular pulses to effect a magnetic field; a probe including the excitor coil for applying to the blood flow an alternative rectangular magnetic field with a non-excitation period interposed between each excitation period and detector electrodes for detecting the induced voltage corresponding to the velocity of the blood flow; ECG signal eliminator circuit means including sample-and-hold circuit means sampling induced voltage output signals of said detector electrodes at the end portion of one of a pair of adjacent non-excitation and excitation periods and holding said sampled signals, means for subtracting each of said sampled signals from each of said output signals for the directly succeeding other of the pair of excitation and non-excitation periods, synchronous detector circuit means detecting the sampled output signals of said subtracting means at a point spaced from the end portion of the succeeding one of excitation and non-excitation periods, and hold circuit means producing the envelope of output signals of said synchronous detector circuit means; transformer-component eliminator circuit means; transformer-component extracting means averagely subtracting output signals of said transformer-component eliminator circuit means from those of said ECG signal eliminator circuit means; and means for subtracting output signals of said transformer-component extracting means from those of said ECG signal eliminator circuit means; said transformer-component eliminator circuit means including means for generating a voltage corresponding to the transformer component $V_{TM}$ of induced voltage output signal of said detector electrodes for each excitation period on the basis of the transformer component $V_T$ of sampled induced voltage output signal of said detector electrodes for each non-excitation period in accordance with the relation $V_T = KV_{TM} + V_O$ (K: the constant of proportion, $V_O$: offset voltage), means for subtracting said voltage $V_{TM}$ from the output signal of said probe directly before or after each excitation period, synchronous detector circuit means detecting the sampled output signals of said subtracting means for each excitation period and hold circuit means producing the envelope of output signals of said synchronous detector circuit means.

2. An electromagnetic blood flowmeter according to claim 1, in which said transformer-component extracting means comprises a first mean value circuit averaging output signals of said ECG signal eliminator circuit means, a second mean value circuit averaging output signals of said transformer-component eliminator circuit means and a subtractor circuit subtracting output signals of said second mean value circuit from those of said first mean value circuit.

3. An electromagnetic blood flowmeter according to claim 1, in which said transformer-component extracting means is composed of a subtractor circuit subtracting output signals of said transformer-component eliminator circuit means from those of said ECG signal eliminator circuit means and a mean value circuit averaging output signals thereof.

* * * * *